United States Patent
Themelis

(10) Patent No.: US 11,536,938 B2
(45) Date of Patent: Dec. 27, 2022

(54) MICROSCOPE SYSTEM AND METHOD FOR CONTROLLING A SURGICAL MICROSCOPE

(71) Applicant: Leica Instruments (Singapore) Pte. Ltd., Singapore (SG)

(72) Inventor: George Themelis, Lindau (DE)

(73) Assignee: LEICA INSTRUMENTS (SINGAPORE) PTE. LTD., Singapore (SG)

( * ) Notice: Subject to any disclaimer, the term of this patent is extended or adjusted under 35 U.S.C. 154(b) by 238 days.

(21) Appl. No.: 15/929,867

(22) Filed: May 27, 2020

(65) Prior Publication Data

US 2020/0409129 A1 Dec. 31, 2020

(30) Foreign Application Priority Data

May 27, 2019 (EP) .................................... 19176723

(51) Int. Cl.
*G02B 21/00* (2006.01)
*G02B 21/36* (2006.01)

(52) U.S. Cl.
CPC ....... *G02B 21/0012* (2013.01); *G02B 21/365* (2013.01)

(58) Field of Classification Search
CPC .. G02B 21/0012; G02B 21/32; G02B 21/365; G06V 40/10; G16H 40/63; G06F 9/455; G06K 17/00; G06N 20/00; A61B 90/20; A61B 34/10; A61B 3/0025; A61B 3/10; A61B 3/13; A61B 3/103; A61F 2/1637
See application file for complete search history.

(56) References Cited

U.S. PATENT DOCUMENTS

| 2016/0081755 A1* | 3/2016 | Wellhöfer | A61B 90/50 606/4 |
|---|---|---|---|
| 2017/0151034 A1 | 6/2017 | Oda et al. | |
| 2018/0130556 A1* | 5/2018 | Dobai | G16H 80/00 |
| 2018/0248972 A1 | 8/2018 | Ahuja | |
| 2018/0326948 A1 | 11/2018 | Cheikh | |

(Continued)

FOREIGN PATENT DOCUMENTS

| DE | 10349419 A1 | 7/2005 |
|---|---|---|
| DE | 102008043534 A1 | 5/2010 |
| JP | 2003-530938 A | 10/2003 |

(Continued)

OTHER PUBLICATIONS

Carl Zeiss Surgical GMBH, OPMI® Pentero® C Software Release 2.20/2.21 Instructions for Use, (Issue 4.2 2009).

*Primary Examiner* — Mustak Choudhury
(74) *Attorney, Agent, or Firm* — 2SPL Patent Attorneys PartG mbB; Yong Beom Hwang

(57) ABSTRACT

Method for automatically setting at least a unit parameter for a medical unit or unit part with parameter values relating to a particular user. According to the method, a user is identified, a corresponding parameter set is selected and unit parameters are set with the selected parameter set. The preceding steps are only implemented when an authentication signal for activating the identification, selection and setting processes is received or present. The authentication signal can be based on use of a user priority database. The invention also relates to a corresponding medical unit and medical system.

11 Claims, 3 Drawing Sheets

(56) References Cited

U.S. PATENT DOCUMENTS

2019/0115108 A1* 4/2019 Hegedus ................ A61B 34/10

FOREIGN PATENT DOCUMENTS

| JP | 2010-088916 A | 4/2010 | | |
|---|---|---|---|---|
| JP | 2015-527913 A | 9/2015 | | |
| JP | 2016-061827 A | 4/2016 | | |
| JP | 2018-105974 A | 7/2018 | | |
| JP | 2019-509072 A | 4/2019 | | |
| WO | 0180739 A1 | 11/2001 | | |
| WO | WO-0180739 A1 * | 11/2001 | ............... | A61B 6/00 |
| WO | 2013099580 A1 | 7/2013 | | |

* cited by examiner

MICROSCOPE SYSTEM AND METHOD FOR CONTROLLING A SURGICAL MICROSCOPE

CROSS-REFERENCE TO RELATED APPLICATIONS

This application claims priority under 35 U.S.C. § 119(a) to European Application No. 19176723.5 filed on May 27, 2019. The contents of the earlier filed application are incorporated by reference herein in their entirety.

TECHNICAL FIELD

The present invention relates to a microscope system, comprising a surgical microscope and a method for controlling a surgical microscope.

BACKGROUND

Surgical microscopes offer a wide range of settings and customizations allowing to be adopted to the needs and preferences of the surgeons. However, the process to adjust an appropriate operational setting and the process of customization to the needs of a specific user remain inherently complex, cumbersome, and time-consuming processes. Even after a surgical microscope has been customized to a specific user, switching and interaction between the customization profiles are still cumbersome in daily work when using the surgical microscope in an operating room (OR).

SUMMARY

Therefore, it is an object of the present invention to provide an improved microscope system comprising a surgical microscope and a method for controlling a surgical microscope.

The afore-mentioned object is achieved by the subject-matter of the independent claims. Preferred embodiments are defined in the dependent claims.

The proposed microscope system comprises a surgical microscope, a memory configured to store a plurality of customization profiles, each customization profile defining at least one predetermined operational setting, a user identification unit configured to detect a user identification, and a processor configured to select one of said plurality of customization profiles based on the detected user identification and to operate the surgical microscope in accordance with the at least one predetermined operational setting defined by the selected customization profile.

The microscope system enables a user who may be a surgeon or a surgical assistant to adjust a predetermined operational setting of the surgical microscope merely by providing a user identification to the microscope system. Thus, the detection of the user identification by means of a user identification unit causes the processor of the microscope system to use a specific customization profile which is stored in a memory and assigned to the customization profile of this specific user. The selected customization profile defines the operational setting which shall be used for the specific user. Accordingly, the user does not have to do more than to input the user identification in order to put the surgical microscope into full operation, i.e. into an operating state which is adopted to the needs and preferences of the user.

The predetermined operational setting defined by a specific customization profile may comprise a plurality of setting parameters which are used to operate the surgical microscope in accordance with the user preferences. These setting parameters may e.g. include parameters directly related to the imaging of an object such as focus or zoom parameters or parameters defining the field of view to be imaged. The setting parameters may e.g. further include parameters which are related to the processing of the captured image, for example parameters determining how the captured image is to be displayed on a monitor. Needless to say, that the afore-mentioned parameters are to be understood only as examples, and the operational setting may comprise any parameter suitable for operating the surgical microscope.

Preferably, the processor is configured to create at least one of the plurality of customization profiles by prompting a user input including customization information. According to this embodiment, the processor provides a setup assistance function which may guide the user to create a specific customization profile according to his or her preferences. This can be achieved by prompting the user to input a customization information into the microscope system, for example by asking questions which may be presented to the user e.g. by means of a graphical user interface.

Further, the processor may be configured to provide a sequence of queries, each query prompting said user input. Such a sequence may comprise a list of questions or options presented to the user, each prompting a corresponding user input to respond thereto choosing a specific configuration. The set of questions or options may be presented in such a way that depending on how the user responds thereto, the user is invited by the processor to set a specific preference or to proceed to the next question or option. An exemplary interaction between the processor and the user may be as follows: Initially, the user wants to know what a specific button to be operated by the user might be used for. For this, the user pushes the button, and then the processor informs the user about the functionality of the button, i.e. a set of available functions. Subsequently, the user wants to set a specific function within the functionality of the button. For example, the user might want to record a specific workflow macro which would allow the user to record a sequence of actions, e.g. switch to fluorescence mode, capture and save three images, and then switch back to the previous imaging mode.

Preferably, the user identification unit comprises one or more sensors (in the following also referred to as sensor means or sensor arrangement) configured to detect the user identification. Such sensor means provide a physical interface between the processor on the one hand and an interface medium on the other hand, wherein said interface medium comprises identification means which are configured to be recognized by the sensor means in order to identify the user before the surgical microscope is put into operation.

The afore-mentioned sensor means may comprise at least one sensor selected from a group including a radio-frequency identification sensor, a code reader, an optical sensor, a microphone, a tactile sensor, a camera, and a touch sensitive screen. In such an embodiment, a suitable interface medium identifying the specific user may be selected dependent on the type of the sensor used for providing the physical interface. For example, an RFID chip may be used as an interface medium in a case in which the sensor is formed by a radio-frequency identification sensor. An RFID chip may be implemented in form of a card permanently used by the specific user, such as a hospital identifier (ID) or an ID specifically issued for an operating room and/or the use of specific medical devices. Alternatively, single use RFID chips may be attached on bracelets which can be worn by the user together with OR clothes which usually are single use articles likewise. As a further alternative, an RFID chip could be embedded within the clothes. In such a case, the user would have to inform the microscope system once that this specific RFID chip is the identifier of the user.

Correspondingly, a QR code may be used as an interface medium in connection with a code reader, e.g. a camera. If the interface medium is formed by a QR code, the latter may already be printed on a hospital ID or attached on the ID in form of a sticker. The QR code may be recognized by a camera on the control panel side of the surgical microscope. Alternatively, the QR code may be printed on the user's clothes on the spot by a printer connected to the surgical microscope.

In case that a microphone is used as the physical interface, the user's voice or the user's hand or finger generating a knock pattern may be used as an interface medium identifying the specific user. The user's hand or finger may be used likewise when the physical interface is formed by a tactile sensor or a touch sensitive screen.

A kind of knocking pattern may also be used by means of keys dedicated to this specific purpose. For instance, keys or buttons located on a handle of the surgical microscope may be clicked simultaneously several times in order to recognize a specific user.

If an optical recognition of the user's hospital ID is applied, the recognition may be performed at the very beginning of the commissioning of the surgical microscope to put the specific user on a list of recent users. When using e.g. a microphone or a tactile sensor, a knock pattern performed by the user on the microscope may be detected likewise. For instance, a user might perform a multiple and then a single knock, and every time the ID is detected, the customization profile changes accordingly.

In a preferred embodiment, the sensor means comprises an optical eye recognition means. Such an optical eye recognition means may be formed e.g. by a camera.

For example, the optical eye recognition means may be included in an optical eyepiece of the surgical microscope. By integrating the optical eye recognition means into the eyepiece, whenever the user approaches the eyepiece of the surgical microscope to look through, the user's eye is recognized thereby identifying the user so that the customization profile associated with the specific user can be selected immediately. Thus, the user does not feel as being forced to take any action in order to be recognized. Operating the surgical microscope becomes very convenient.

Preferably, the sensor means may comprise at least a first sensor and a second sensor, wherein at least one of the plurality of customization profiles includes at least a first operational setting and a second operational setting. Further, the processor may be configured to select the first operational setting if the user input is detected by the first sensor and to select the second operational setting if the user input is detected by the second sensor. In such an embodiment, the surgical microscope may have multiple sensors such as RFID (contactless) readers, cameras, and microphones. Depending on which sensor is used to be recognized, a different operational setting within the customization profile associated with the specific user will be selected. For example, the surgical microscope may have two RFID readers on both sides of an optics carrier, and the customization profile may be programmed for the specific user such that by identifying the user by means of the RFID reader located on the right side, a first operational setting may be selected which is e.g. the default setting of the recognized user. In contrast, if the user is identified by the RFID reader on the left side, a current operational setting may be applied for the recognized user, i.e. the user adopts the current setting. Needless to say, that a plurality of different combinations of recognition actions may be programmed to perform specific functions or macros.

According to a preferred embodiment, the processor is configured to create the at least one of the plurality of customization profiles based on a machine learning algorithm. The machine learning algorithm may be programmed such that the microscope system successively learns with continued use enabling the microscope system to offer options which are likely to be selected based on previous use. For instance, the microscope system may use the machine learning algorithm to learn that certain users work together. Thus, when a specific user is already working with the surgical microscope, the customization profile of another user may be offered. According to another example, the microscope system may learn that in case a specific user tries to focus longer than a typical duration, it is likely that the user might also want to capture and save images. Accordingly, an option to capture and save images may be offered automatically to the user.

Preferably, the processor may be configured to merge at least two of the plurality of customization profiles, which are assigned to different user information, into a common customization profile. In such a manner, a team of users may be defined wherein each user of the team is allowed to rely on all customization profiles which have been created for other users of the team. This embodiment may be advantageously combined with the machine learning algorithm based on which the team of users may be composed.

Preferably, the processor may be configured to detect a user actuation during operation of the surgical microscope and to modify the at least one of the plurality of customization profiles based on the detected user actuation. Also, such an embodiment may be advantageously combined with the machine learning algorithm.

According to another aspect, a method and corresponding computer program for controlling a surgical microscope is provided, comprising the following steps: providing a plurality of customization profiles, each customization profile defining at least one predetermined operational setting; detecting a user identification; selecting one of said plurality of customization profiles based on the detected user identification; and operating the surgical microscope in accordance with the at least one predetermined operational setting defined by the selected customization profile.

BRIEF DESCRIPTION OF THE FIGURES

Hereinafter, specific embodiments are described referring to the drawings, in which.

DETAILED DESCRIPTION

Figure 1:
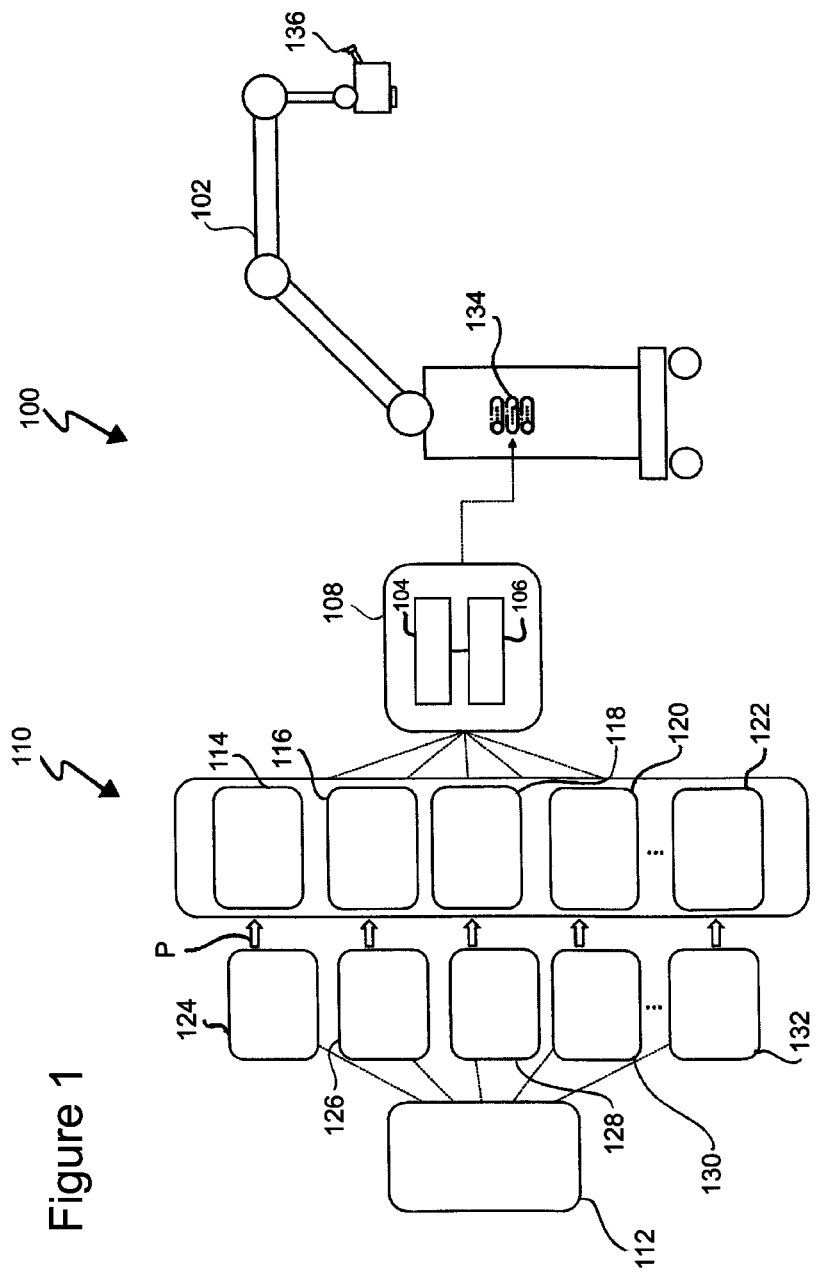
FIG. 1 is a diagram showing a microscope system according to an embodiment.

FIG. 1 is a schematic diagram showing a microscope system 100 according to an embodiment. The microscope system 100 comprises a surgical microscope 102 typically operated by a surgeon and/or an assistant in an operating room to perform surgery on a patient, such as brain, eye, or spine surgery. The microscope system 100 further comprises a processor 104 and a memory 106 which may be part of control unit 108. The control unit 108 may be formed by a computer device.

The control unit 108 comprising the processor 104 and the memory 106 is coupled to a user identification unit 110 which is configured to detect a user identification authorizing the user (e.g. a surgeon or nurse) designated by 112 in FIG. 1. The user identification unit 110 comprises sensor means e.g. in form of a plurality of sensors 114, 116, 118, 120, 122. The user identification unit 110 further comprises identification means e.g. in form of a plurality of interface media 124, 126, 128, 130, 132. According to the present embodiment, each of the plurality of sensors 114 to 122 is configured to interact with one of the interface media 124 to 132 as illustrated by arrows P in FIG. 1. As described later in detail, each interface medium 124 to 132 comprises an identification means which is configured to be recognized by the associated sensor 114 to 122 in order to identify the user before the surgical microscope 102 is put into operation. Generally speaking, the sensor means formed by the plurality of sensors 114 to 122 provides a physical interface between the control unit 108 on the one hand and the associated interface media 124 to 132 on the other hand.

The memory 106 is configured to store a plurality of customization profiles. Each of the customization profiles stored in the memory 106 defines at least one predetermined operational setting according to which the surgical microscope 102 operates once the surgical microscope 102 is put into operation after the user 112 has been identified by means of the user identification unit 110. For illustrative purposes only, the different operational settings are referred to with reference sign 134 in FIG. 1.

The processor 104 is configured to select one of the plurality of customization profiles based on the user identification which is provided by one of the interface media 124 to 132 and detected by the associated sensor 114 to 122. Among the plurality of customization profiles stored in the memory 106, the processor 104 selects the one profile which belongs to the specific user recognized by the user identification. With selecting this customization profile, the user is enabled to operate the surgical microscope 102 in accordance with the operational setting defined by the selected customization profile.

Figure 2:
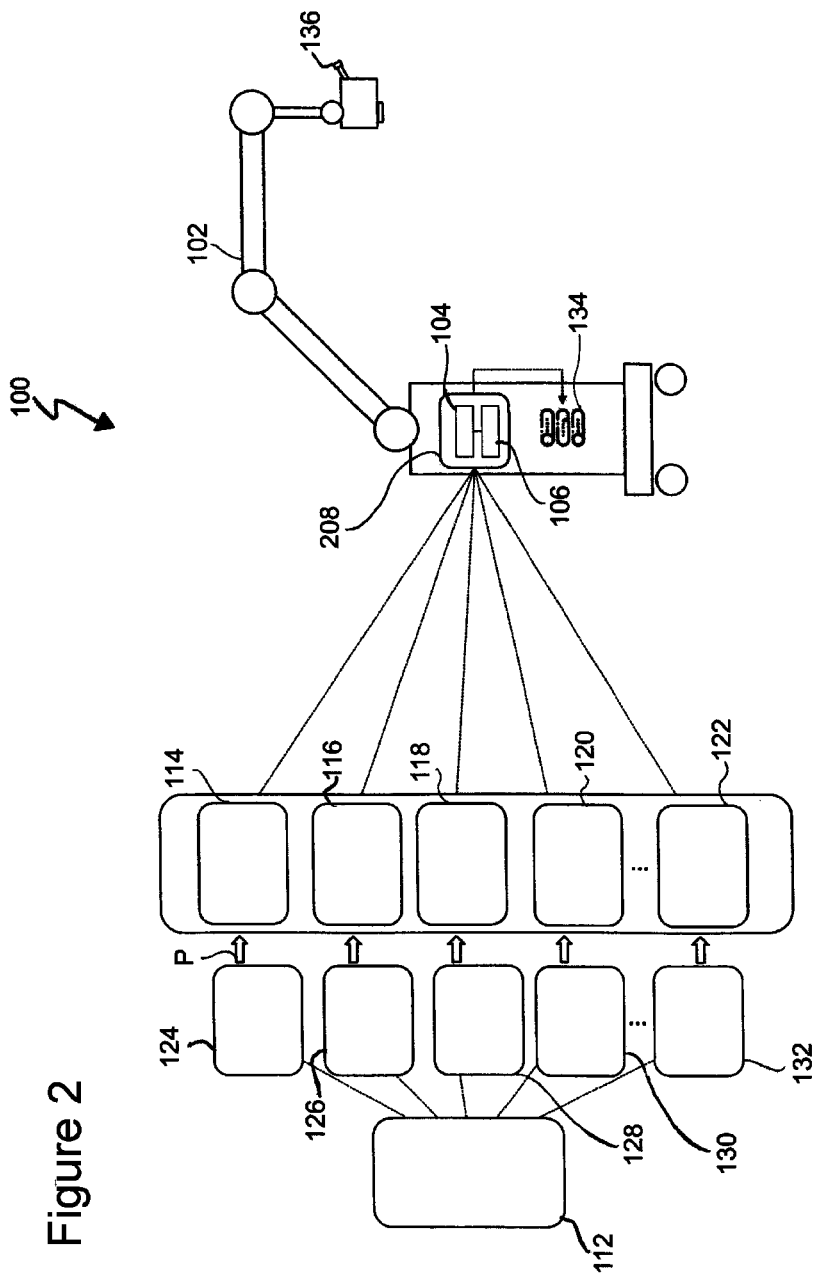
FIG. 2 is a diagram showing the microscope system according to a modified embodiment.

FIG. 2 illustrates a modification of the embodiment shown in FIG. 1. Whereas according to the embodiment in FIG. 1, the control unit 108 including the processor 104 and the memory 106 is formed by a component physically separated from the surgical microscope, the modified configuration of FIG. 2 includes a control unit 208 which is integrated with the surgical microscope 102. Again, the control unit 208 includes the processor 104 and the memory 106. Apart from the afore-mentioned modification, the configurations illustrated in FIGS. 1 and 2 are identical.

Figure 3:
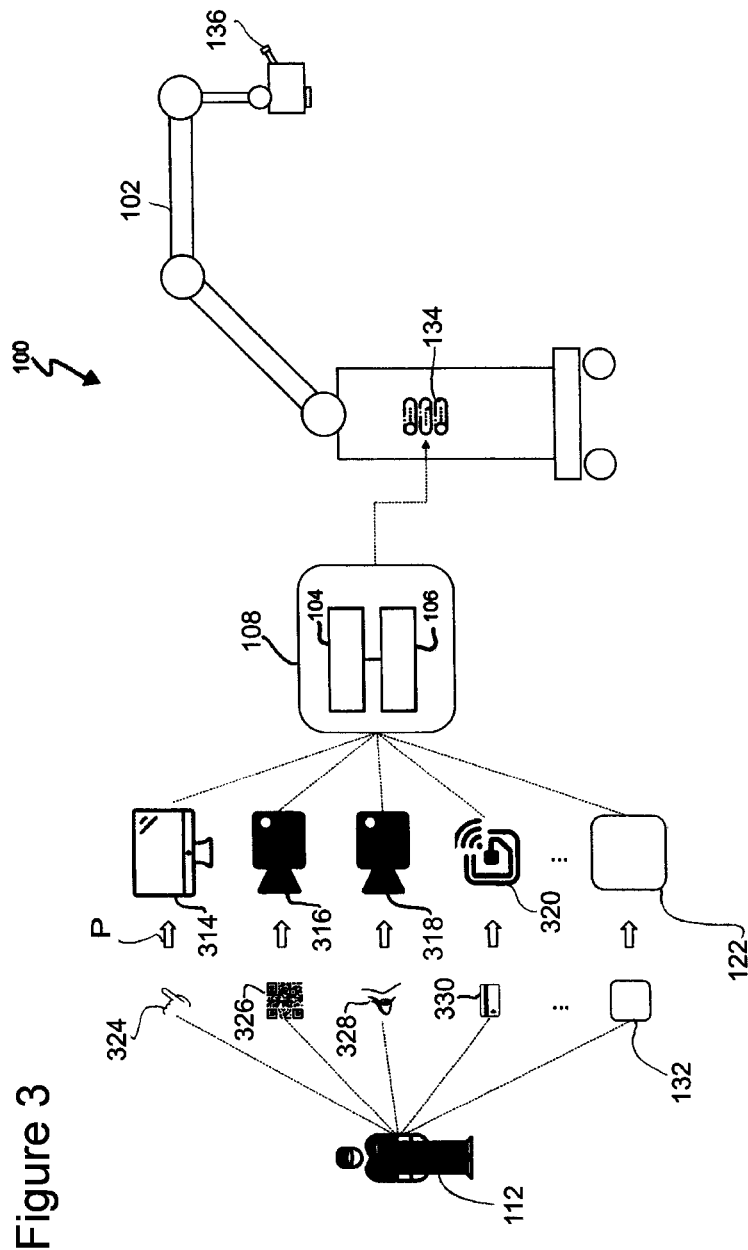
FIG. 3 is a diagram showing the microscope system of FIG. 1 including a specific embodiment of a user identification unit.

FIG. 3 shows an exemplary configuration which is based on the embodiment of FIG. 1. This exemplary configuration shall illustrate which types of sensors and associated interface media may be used to form the sensor means for identifying the user. Thus, the sensor means of the user identification unit 110 may comprise a touch sensitive screen 314 (corresponding to sensor 114 in FIG. 1) interacting with a hand or a finger 324 of the user (corresponding to interface medium 124 in FIG. 1). Further, the sensor means may comprise a first camera 316 (corresponding to sensor 116 in FIG. 1) interacting with a QR code 326 (corresponding to interface medium 126 in FIG. 1). The sensor means may further comprise a second camera 318 (corresponding to sensor 118 in FIG. 1) interacting with a user's eye 328 (corresponding to interface medium 128 in FIG. 1). The sensor means may further comprise an RFID (contactless) reader 320 (corresponding to sensor 120 in FIG. 1) interacting with an RFID (contactless) chip 330 (corresponding to interface medium 130 in FIG. 1).

Needless to say that the sensors 314 to 320 are merely examples, and any other types of sensors and interface media may be used provided that these sensors and interface media are suitable to detect a user identification based on which the specific user can be recognized. Further, it goes without saying that the configuration shown in FIG. 3 may also be based on the embodiment of FIG. 2.

Further, according to FIGS. 1 to 3, the sensors 114 to 122 and 314 to 320, respectively, are illustrated as being physically separated from the surgical microscope 102. However, this illustration serves only to simplify the diagrams. Needless to say, that the sensors 114 to 122, 314 to 320 may also be integrated with the surgical microscope 102. For example, the camera 318 recognizing the user's eye 328 may be integrated into an eyepiece 136 of the surgical microscope.

Further, the sensor means shown in FIGS. 1 to 3 comprises a plurality of sensors 114 to 122, 314 to 320 and associated interface media 124 to 132, 324 to 330. However, it is also possible to use one single sensor as well as one single interface medium associated therewith, though providing more than one of the afore-mentioned components may have some benefits. For instance, assumed that the sensor means comprises at least a first sensor and a second sensor, both of which being formed by an RFID chip, it may be possible that the processor 104 is configured to select a first operational setting if the user input is detected by the first sensor, and to select the second operational setting if the user input is detected by the second sensor. The first and second operational settings may be included in a single customization profile belonging to the specific user. Thus, by selecting one of the two RFID readers, the user is enabled to select the corresponding operational setting associated with the selected RFID reader.

As explained above, the processor 104 serves to select the customization profile based on an identification of the user 112 and to operate the surgical microscope 102 in accordance with the operational setting which is defined by the selected customization profile. However, the processor 104 may not be limited to the afore-mentioned function. For example, the processor 104 may further be configured to provide a setup assistance function guiding the user 112 in a process for creating a specific customization profile according to his or her preferences, this profile being storable in the memory 106. For this, the processor 104 may be configured to prompt the user 112 to input customization information. For instance, the processor 104 may cause a display device (not shown in the Figures) to present questions or options to which the user 112 can respond to in order to create the desired profile. The processor 104 may e.g. provide a sequence of queries, each query prompting a user input based on which the customization profile can be created.

The processor 104 may further be configured to apply a machine learning algorithm. Using such a machine learning algorithm, the processor 104 may create the customization profiles to be stored in the memory 106. The processor 104 may also be configured to merge at least two customization profiles, which are assigned to different user information, i.e. to different users, into a common customization profile to be stored in the memory 106. Such a configuration has its benefits in case that a team of users is working with the surgical microscope 102, and each user of the team shall have the possibility of also using the profiles of the other users.

Further, the processor 104 may be configured to detect a user actuation during operation of the surgical microscope 102 in order to modify the customization profile belonging to this user based on the detected user actuation. Also, for such a configuration, the processor 104 may advantageously use the machine learning algorithm.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer, or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine-readable carrier.

Other embodiments comprise the computer program for performing one of the methods described herein, stored on a machine-readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device, or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

LIST OF REFERENCE SIGNS 100 microscope system
102 surgical microscope
104 processor
106 memory
108 control unit
110 user identification unit
112 user
114 to 122 sensor
124 to 132 interface medium
134 operational setting
136 optical eyepiece
208 control unit
314 touch sensitive screen
316 camera
318 camera
320 RFID reader
324 hand/finger
326 QR code
328 user's eye
330 RFID chip
P arrows

What is claimed is:

1. A microscope system, comprising:
a surgical microscope,
a memory configured to store a plurality of custom profiles, each custom profile defining at least one predetermined operational setting of the surgical microscope according to which the surgical microscope operates once the surgical microscope is put into operation,
a user identification unit configured to detect a user identification, and
a processor configured to select one of said plurality of custom profiles based on the detected user identification and to put the surgical microscope into operation in accordance with the at least one predetermined operational setting defined by the selected custom profile,
wherein the user identification unit comprises one or more sensors configured to detect the user identification, wherein the one or more sensors comprise at least a first sensor and a second sensor, and at least one of the plurality of custom profiles includes at least a first operational setting and a second operational setting, wherein the processor is configured to select the first operational setting if the user identification is detected by the first sensor and select the second operational setting if the user identification is detected by the second sensor.

2. The microscope system according to claim 1, wherein the processer is configured to create at least one of the plurality of profiles by prompting a user input including customization information.

3. The microscope system according to claim 1, wherein the processor is configured to provide a sequence of queries, each query prompting said user input.

4. The microscope system according to claim 1, wherein the one or more sensors comprise at least one sensor selected from a group including a radio-frequency identification sensor, a code reader, an optical sensor, a microphone, a tactile sensor, a camera, and a touch sensitive screen.

5. The microscope system according to claim 1, wherein the one or more sensors comprise an optical eye recognition means.

6. The microscope system to claim 5, wherein the optical eye recognition means is included in an optical eyepiece of the surgical microscope.

7. The microscope system according to claim 1, wherein the processor is configured to create the at least one of the plurality of custom profiles based on a machine learning algorithm.

8. The microscope system according to claim 1, wherein the processor is configured to merge at least two of the plurality of custom profiles, which are assigned to different user information, into a common custom profile.

9. The microscope system according to claim 1, wherein the processor is configured to detect an actuation by a user to modify the custom profile of the user during operation of the surgical microscope and to modify the custom profiles of the user based on the detected actuation.

10. A method for controlling a surgical microscope, the method comprising:
    providing a plurality of custom profiles, each custom profile defining at least one predetermined operational setting of the surgical microscope according to which the surgical microscope operates once the surgical microscope is put into operation,
    detecting, by a user identification unit, a user identification,
    selecting one of said plurality of custom profiles based on the detected user identification, and
    putting the surgical microscope into operation in accordance with the at least one predetermined operational setting defined by the selected custom profile,
    wherein the user identification unit comprises one or more sensors configured to detect the user identification,
    wherein the one or more sensors comprise at least a first sensor and a second sensor, and at least one of the plurality of custom profiles includes at least a first operational setting and a second operational setting,
    wherein the first operational setting is selected if the user identification is detected by the first sensor, and the second operational setting is selected if the user identification is detected by the second sensor.

11. A non-transitory storage medium having electronically readable control signals stored thereon, which cooperate with a programmable computer system such that the method of claim 10 for controlling a surgical microscope is performed.

* * * * *